United States Patent
Yamanouchi et al.

(10) Patent No.: US 11,457,938 B2
(45) Date of Patent: Oct. 4, 2022

(54) FOREIGN SUBSTANCE REMOVING DEVICE AND FOREIGN SUBSTANCE COLLECTING SYSTEM

(71) Applicants: KAWASUMI LABORATORIES, INC., Saiki (JP); Dai Yamanouchi, Verona, WI (US)

(72) Inventors: Dai Yamanouchi, Verona, WI (US); Kunihiro Ohta, Tokyo (JP); Hiroki Ishida, Bungo-ono (JP)

(73) Assignees: KAWASUMI LABORATORIES, INC., Saiki (JP); Dai Yamanouchi, Verona, WI (US)

( * ) Notice: Subject to any disclaimer, the term of this patent is extended or adjusted under 35 U.S.C. 154(b) by 85 days.

(21) Appl. No.: 16/484,702

(22) PCT Filed: Feb. 9, 2018

(86) PCT No.: PCT/JP2018/004741
§ 371 (c)(1),
(2) Date: Aug. 8, 2019

(87) PCT Pub. No.: WO2018/147449
PCT Pub. Date: Aug. 16, 2018

(65) Prior Publication Data
US 2020/0187966 A1    Jun. 18, 2020

(30) Foreign Application Priority Data
Feb. 10, 2017 (JP) .............................. JP2017-022993

(51) Int. Cl.
*A61B 17/221* (2006.01)

(52) U.S. Cl.
CPC .... *A61B 17/221* (2013.01); *A61B 2017/2212* (2013.01)

(58) Field of Classification Search
CPC . A61B 17/221; A61B 2017/2212; A61F 2/01; A61F 2/0108; A61F 2/011; A61F 2002/016; A61F 2002/018
(Continued)

(56) References Cited

U.S. PATENT DOCUMENTS

| 6,099,534 A * | 8/2000 | Bates ................... A61B 17/221 606/127 |
| 7,169,154 B1 | 1/2007 | Que et al. |

(Continued)

FOREIGN PATENT DOCUMENTS

| JP | 2004-298637 A | 10/2004 |
| JP | 2006-87473 A | 4/2006 |

(Continued)

OTHER PUBLICATIONS

Written Opinion (PCT/ISA/237) issued by the International Searching Authority in corresponding International Application No. PCT/JP2018/004741, dated May 1, 2018.
(Continued)

*Primary Examiner* — Kathleen S Holwerda
*Assistant Examiner* — Kankindi Rwego
(74) *Attorney, Agent, or Firm* — Sughrue Mion, PLLC

(57) ABSTRACT

A foreign substance removing device includes a tubular member and a retriever configured to be expandable to and contractible from a predetermined shape. The retriever includes main wires disposed to be centered around a tube axis of the tubular member, and sub wires each connecting adjacent ones of the main wires to each other. Each of the main wires is configured to curve when the retriever is expanded such that a space having a predetermined size is provided by the main wires. Each of the sub wires is configured to be foldable at at least one point between the adjacent ones of the main wires. When the retriever is
(Continued)

expanded, the folding points of the sub wires are positioned inside the space such that the sub wires do not protrude out of the main wires.

6 Claims, 14 Drawing Sheets

(58) Field of Classification Search
 USPC .......................................................... 606/159
 See application file for complete search history.

(56) References Cited

U.S. PATENT DOCUMENTS

| | | | |
|---|---|---|---|
| 2004/0087999 | A1 | 5/2004 | Bosma et al. |
| 2004/0088001 | A1 | 5/2004 | Bosma et al. |
| 2004/0199201 | A1* | 10/2004 | Kellett ............... A61B 17/221 606/200 |
| 2005/0015111 | A1* | 1/2005 | McGuckin, Jr. ......... A61F 2/01 606/200 |
| 2005/0080449 | A1 | 4/2005 | Mulder |
| 2005/0267491 | A1 | 12/2005 | Kellett et al. |
| 2007/0135820 | A1 | 6/2007 | Que et al. |
| 2010/0268265 | A1* | 10/2010 | Krolik ............... A61B 17/221 606/200 |
| 2011/0143903 | A1 | 6/2011 | Que et al. |
| 2012/0059356 | A1* | 3/2012 | di Palma ............. A61B 17/221 604/509 |
| 2014/0052103 | A1 | 2/2014 | Cully et al. |
| 2014/0052161 | A1 | 2/2014 | Cully et al. |
| 2015/0173783 | A1 | 6/2015 | Tah et al. |
| 2016/0038174 | A1 | 2/2016 | Bruzzi et al. |
| 2016/0120571 | A1 | 5/2016 | Cully et al. |
| 2016/0183965 | A1 | 6/2016 | Cully et al. |
| 2016/0206344 | A1 | 7/2016 | Bruzzi et al. |
| 2017/0150986 | A1 | 6/2017 | Cully et al. |
| 2018/0271556 | A1 | 9/2018 | Bruzzi et al. |
| 2019/0046227 | A1 | 2/2019 | Cully et al. |

FOREIGN PATENT DOCUMENTS

| | | |
|---|---|---|
| JP | 2006-521865 A | 9/2006 |
| JP | 2007-252518 A | 10/2007 |
| JP | 2008-272501 A | 11/2008 |
| JP | 2009-165751 A | 7/2009 |
| JP | 2015-524735 A | 8/2015 |
| JP | 2016-513524 A | 5/2016 |
| JP | 2017-500156 A | 1/2017 |

OTHER PUBLICATIONS

International Search Report (PCT/ISA/210), issued by International Searching Authority in corresponding International Application No. PCT/JP2018/004741, dated May 1, 2018.

Office Action dated Apr. 26, 2022 by the Japanese Patent Office in counterpart Japanese Patent English Application No. 2018-567532.

\* cited by examiner

FOREIGN SUBSTANCE REMOVING DEVICE AND FOREIGN SUBSTANCE COLLECTING SYSTEM

TECHNICAL FIELD

The present invention relates to a foreign substance removing device, a foreign substance removing catheter, and a foreign substance collecting system, and more particularly, to a foreign substance removing device, a foreign substance removing catheter, and a foreign substance collecting system for removing or collecting foreign substance such as a thrombus or an embolus generated in a tubular tissue such as a blood vessel.

BACKGROUND ART

As shown in FIG. 15 a thrombectomy device 900 including a radially expandable cage 922 is known as a thrombectomy device for removing a thrombus from a blood vessel wall (see, e.g., Patent Literature 1). The cage 922 is disposed at tip end positions of tubular members that are respectively referred to as a proximal arm and a distal arm (not shown), and are configured such that a radial length of the 922 is adjustable by moving the proximal arm and the distal arm relative to each other along an axial direction. A flat wire 924 is attached to the cage 922, and the flat wire 924 can scrape thrombus from the blood vessel wall.

PRIOR ART DOCUMENT

Patent Literature

Patent Literature 1: JP2016-513524A

SUMMARY OF INVENTION

Technical Problem

However, in the thrombectomy device disclosed in the above Patent Literature 1, since a folding point 924F of the flat wire 924 greatly protrudes out of the cage 922, if the cage 922 is rotated or the cage 922 is moved forward or backward within the blood vessel in a state where the cage 922 is expanded, the folding point 924F of the flat wire 924 may hit the blood vessel wall and damage the blood vessel wall.

Such a problem can also occur in a foreign substance removing device that removes foreign substance generated inside a tubular tissue other than a blood vessel (e.g., a gastrointestinal tract, a bile duct, or the like).

The present invention has been made in view of the problem described above, and an object thereof is to provide a foreign substance removing device, a foreign substance removing catheter, and a foreign substance collecting system for removing or collecting foreign substance generated in a tubular tissue while reducing a risk of damaging the tubular tissue.

Solution to Problem

The object of the present invention is achieved by the following configurations.
(1) A foreign substance removing device for removing a foreign substance in a body lumen, the foreign substance removing device including: a tubular member; and a retriever disposed in a portion of the tubular member and configured to be expandable to and contractible from a predetermined shape, in which the retriever includes a plurality of main wires disposed to be centered around a tube axis of the tubular member, and a plurality of sub wires each connecting adjacent ones of the main wires to each other, in which each of the plurality of main wires is configured to curve when the retriever is expanded such that a space having a predetermined size is provided by the plurality of main wires, in which each of the plurality of sub wires is configured to be foldable at at least one point between the adjacent ones of the main wires, and in which, when the retriever is expanded, folding points of the sub wires are positioned inside the space such that the sub wires do not protrude out of the plurality of main wires.
(2) The foreign substance removing device according to (1), in which the retriever further includes a plurality of regulating portions connected to the folding points of the sub wires to regulate positions of the folding points such that, when the retriever is expanded, the folding points do not protrude out of the plurality of main wires.
(3) The foreign substance removing device according to (2), in which each of the plurality of sub wires is configured to be foldable such that a pair of arm portions extending away from each other from the folding point toward the adjacent ones of the main wires move toward each other, and is arranged to be convex from an intermediate portion of the retriever toward an end portion of the retriever, and in which each of the plurality of regulating portions connects the folding point of a corresponding one of the sub wires and the end portion of the retriever to each other.
(4) The foreign substance removing device according to any one of (1) to (3), in which when the retriever is viewed from a direction orthogonal to the tube axis of the tubular member, a part of the plurality of sub wires arranged in a first region from an intermediate portion of the retriever to one end portion of the retriever and another part of the plurality of sub wires arranged in a second region from the intermediate portion of the retriever to another end portion of the retriever are symmetrical with respect to the intermediate portion of the retriever.
(5) The foreign substance removing device according to any one of (1) to (4), in which a rigidity of the main wires is higher than a rigidity of the sub wires.
(6) The foreign substance removing device according to any one of (1) to (5), in which the shape of the retriever upon expansion is spherical or prolate.
(7) A foreign substance removing catheter for removing a foreign substance in a body lumen, the foreign substance removing catheter including: a catheter body; the foreign substance removing device according to any one of (1) to (6) disposed at a distal portion of the catheter body; and an operation portion disposed at a proximal portion of the catheter body to operate the retriever of the foreign substance removing device to expand and contract.
(8) A foreign substance collecting system for collecting a foreign substance in a body lumen, the foreign substance collecting system including: the foreign substance removing catheter according to (7); and a foreign substance capturing catheter to capture the foreign substance in the body lumen, in which the foreign substance capturing catheter includes a lumen through which the foreign substance removing catheter is passed.

Advantageous Effects of Invention

According to the foreign substance removing device described in (1), the plurality of main wires are configured to provide a space having a predetermined size when the retriever is expanded, and the folding points of the sub wires are positioned inside the space so that the sub wires do not protrude out of the main wires when the retriever is expanded. Therefore, even if the retriever is rotated in a state where the retriever is expanded or the retriever is moved forward or backward within the tubular tissue, the folding points of the sub wires are unlikely to be caught in the tubular tissue. As a result, it is possible to remove or collect the foreign substance generated in the tubular tissue while reducing a risk of damaging the tubular tissue.

According to the foreign substance removing device described in (2), since the plurality of regulating portions are provided, the positions of the folding points of the sub wires can be kept inside the space so that the sub wires do not protrude out of the main wires when the retriever is expanded. As a result, the risk of damaging the tubular tissue can be further reduced.

According to the foreign substance removing device described in (3), each of the plurality of sub wires is configured to be foldable such that the pair of arm portions extending from the folding point move toward each other (in other words, in a substantially V shape), and the folding points of the sub wire and the end portions of the retriever are connected to each other by the plurality of regulating portions. Therefore, a foreign substance removing device capable of reducing the risk of damaging the tubular tissue can be realized with a simple configuration.

According to the foreign substance removing device described in (4), since the plurality of sub wires arranged in the first region and in the second region are symmetrical with respect to the intermediate portion of the retriever, the retriever can be expanded uniformly, and the foreign substance in the tubular tissue can be removed or collected effectively.

When the rigidity of the main wires is extremely lower than the rigidity of the sub wires, there may be some drawbacks when the retriever is expanded, for example, the main wires is be expanded as expected, and intervals between the adjacent main wires are not uniform. Regarding this, according to the foreign substance removing device described in (5), since the rigidity of the main wires is higher than the rigidity of the sub wires, it is possible to prevent occurrence of the drawbacks described above. That is, the foreign substance removing device described in (5) is an excellent foreign substance removing device capable of easily expanding the main wires as expected and maintaining a uniform interval between the adjacent main wires.

According to the foreign substance removing device described in (6), since the shape of the retriever upon expansion is spherical or prolate, the expanded retriever is further fitted to the tubular tissue having a circular cross section. As a result, foreign substance sticking to an inner wall of the tubular tissue can be removed effectively.

The foreign substance removing catheter described in (7) includes the foreign substance removing device of the present invention described above, and thus is a foreign substance removing catheter capable of removing or collecting foreign substance generated in a tubular tissue while reducing a risk of damaging the tubular tissue.

The foreign substance collecting system described in (8) includes the foreign substance removing catheter of the present invention described above, and thus is a foreign substance collecting system capable of removing or collecting foreign substance generated in a tubular tissue while reducing a risk of damaging the tubular tissue.

DESCRIPTION OF EMBODIMENTS

Figure 1:
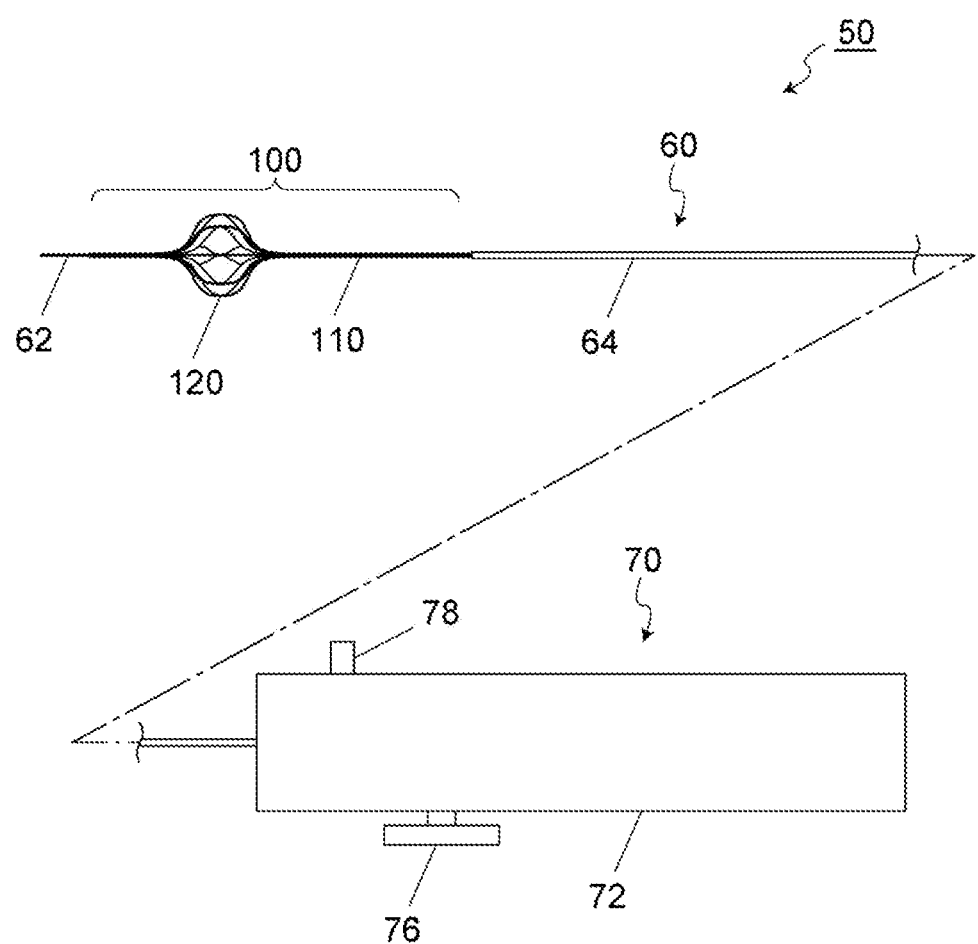
FIG. 1 is a diagram showing a foreign substance removing catheter according to a first embodiment.

Hereinafter, a foreign substance removing device, a foreign substance removing catheter, and a foreign substance collecting system of the present invention will be described based on an embodiment shown in the drawings.

First Embodiment

In the first embodiment, as an example of the foreign substance removing device and the foreign substance that remove catheter of the present invention, a thrombectomy device and a thrombectomy catheter that removes foreign substance such as a thrombus or an embolus generated in a blood vessel will be described as examples.

Figure 2A:
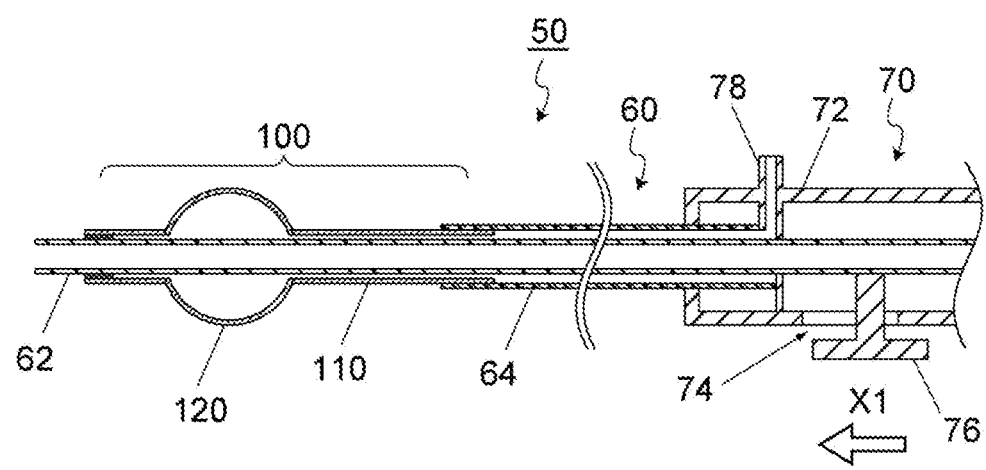
FIG. 2A is a diagram schematically showing an internal structure of a foreign substance removing catheter when a retriever is expanded.
Figure 2B:
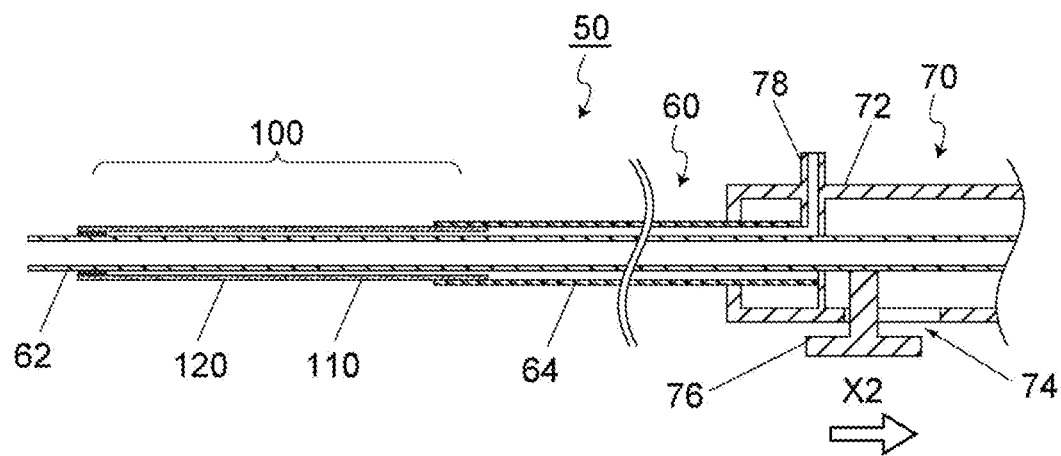
FIG. 2B is a diagram schematically showing an internal structure of a foreign substance removing catheter when a retriever is contracted.

FIG. 1 is a diagram showing a foreign substance removing catheter 50 according to the first embodiment. FIGS. 2A and 2B are diagrams schematically showing an internal structure of the foreign substance removing catheter 50. FIG. 2A is shows the internal structure of the foreign substance removing catheter 50 when a retriever 120 is expanded, and FIG. 2B shows the internal structure of the foreign substance removing catheter 50 when the retriever 120 is contracted. For the purpose of facilitating the understanding of the present invention, in FIGS. 2A and 2B, the lengths, wall thicknesses, and the like of components of the foreign substance removing catheter 50 are shown in an exaggerated manner.

As shown in FIGS. 1, 2A and 2B, the foreign substance removing catheter 50 according to the first embodiment includes: a catheter body 60; a foreign substance removing device 100 disposed at a distal portion of the catheter body 60; and an operation portion 70 disposed at a proximal portion of the catheter body 60. The foreign substance removing catheter 50 is a thrombectomy catheter that removes foreign substance such as a thrombus or an embolus generated in a blood vessel.

In the present description, the term "distal portion" refers to an end portion that is farther from a user of the foreign substance removing catheter 50, and the term "proximal portion" refers to an end portion closer to the user of the foreign substance removing catheter 50.

As shown in FIGS. 2A and 2B, the catheter body 60 includes a first tube 62 extending from a distal portion to a proximal portion of the catheter body 60, and a second tube 64 connecting the foreign substance removing device 100 and the operation portion 70. A guide wire lumen that allows a guide wire to be inserted is provided in the first tube 62. As shown in FIGS. 2A and 2B, an end portion on a distal side of the foreign substance removing device 100 is connected to an outer peripheral surface of a distal portion of the first tube 62, and an end portion on a proximal side of the foreign substance removing device 100 is connected to an inner peripheral surface of a distal portion of the second tube 64. An inner diameter of the second tube 64 is set larger than an outer diameter of the first tube 62, and a gap of a predetermined size is provided between the first tube 62 and the second tube 64.

The first tube 62 and the second tube 64 are both formed of a flexible material. As the flexible material, for example, a synthetic resin (elastomer), a resin compound which is a mixture of a synthetic resin and other materials, a multi-layered structure in which multiple layers of synthetic resin are stacked, or a composite of a synthetic resin and a metal wire can be preferably used.

The operation portion 70 includes, for example, a stick-shaped (rod-shaped) operation body 72, a slider 76 installed on a side surface of the operation body 72, and a liquid injection port 78 provided on the side surface of the operation body 72.

A slot 74 extending in a longitudinal direction (a tube axis direction) is provided on the side surface of the operation body 72. The slider 76 is connected to the first tube 62 via the slot 74, and is configured to be movable in parallel along the longitudinal direction (the tube axis direction).

The liquid injection port 78 is in communication with an internal lumen of the second tube 64 (the gap between the first tube 62 and the second tube 64) and is configured such that a liquid such as saline, for example, can be charged into in the catheter body 60 via the liquid injection port 78. Although not shown in the drawings, an opening of the liquid injection port 78 can be closed in a liquid-tight manner by a closing member such as a cap or a valve made of a silicon rubber or the like.

Here, movement of the foreign substance removing device 100 when the slider 76 is moved will be described with reference to FIGS. 2A and 2B. First, in a state shown in FIG. 2A, when the slider 76 is moved in a direction of an arrow X1, the first tube 62 connected to the slider 76 also moves in the X1 direction. At this time, a connection position between the first tube 62 and the foreign substance removing device 100 moves in the X1 direction, but a connection position between the foreign substance removing device 100 and the second tube 64 does not change. That is, as a result of movement of the first tube 62 relative to the second tube 64 in the X1 direction, the retriever 120 contracts (see FIG. 2B). First, in a state shown in FIG. 2B, when the slider 76 is moved in a direction of an arrow X2, the first tube 62 connected to the slider 76 also moves in the X2 direction. At this time, a connection position between the first tube 62 and the foreign substance removing device 100 moves in the X2 direction, but a connection position between the foreign substance removing device 100 and the second tube 64 does not change. That is, as a result of movement of the first tube 62 relative to the second tube 64 in the X2 direction, the retriever 120 expands (see FIG. 2A). In other words, by moving the slider 76 in parallel along the longitudinal direction (the tube axis direction), expansion and contraction of the retriever 120, which will be described later, can be operated.

Next, a configuration of the foreign substance removing device 100 according to the first embodiment of the invention will be described with reference to FIGS. 3 to 6.

Figure 3:
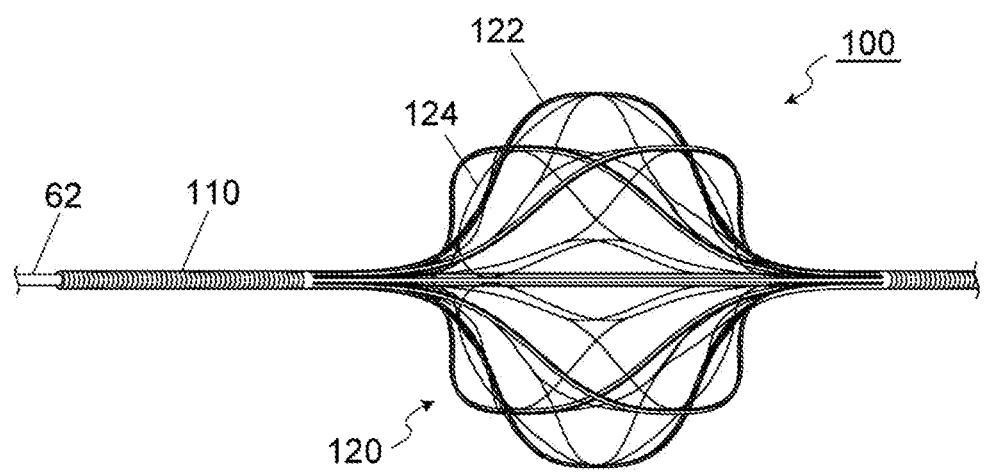
FIG. 3 is an enlarged perspective view of the foreign substance removing device according to the first embodiment.
Figure 4A:
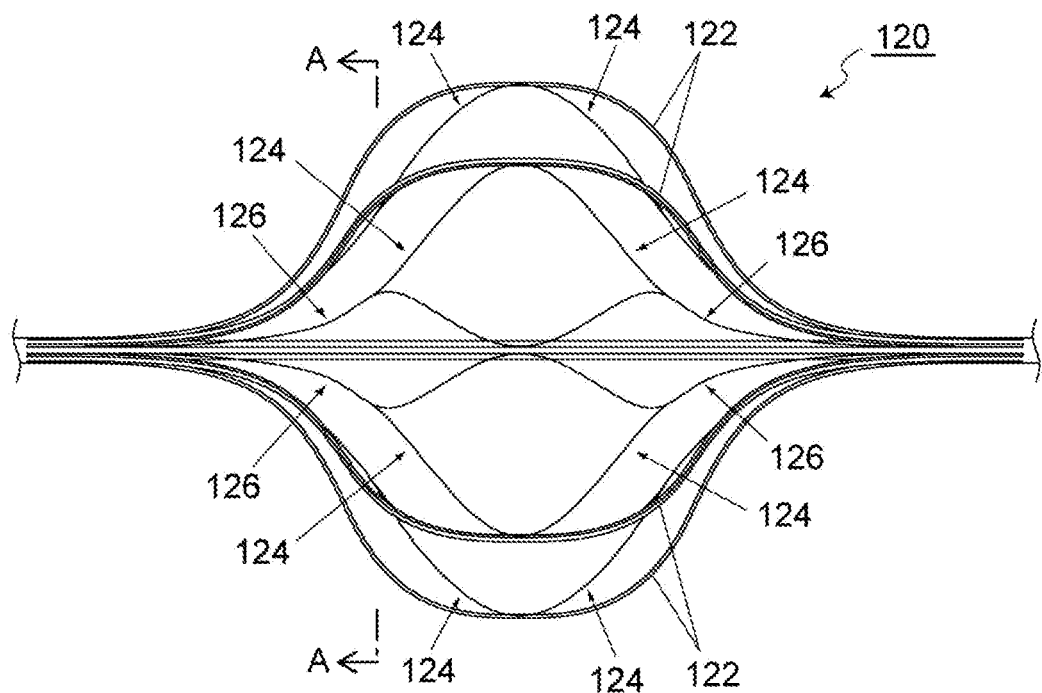
FIG. 4A is an enlarged front view of a retriever.
Figure 4B:
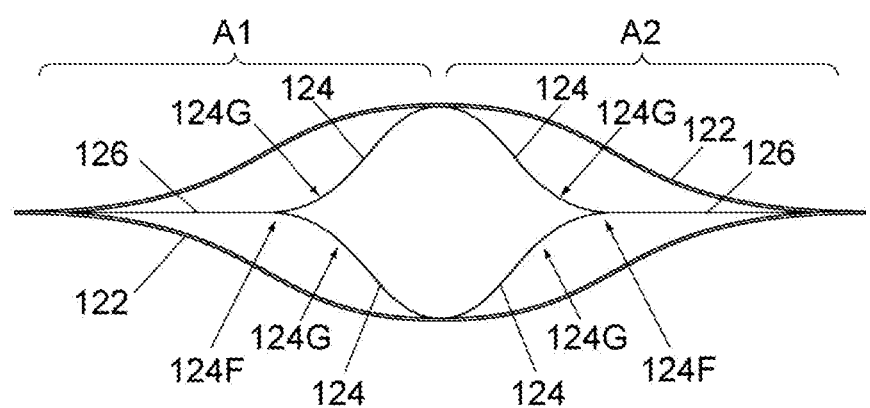
FIG. 4B is a diagram showing an arrangement pattern of sub wires.
Figure 5:
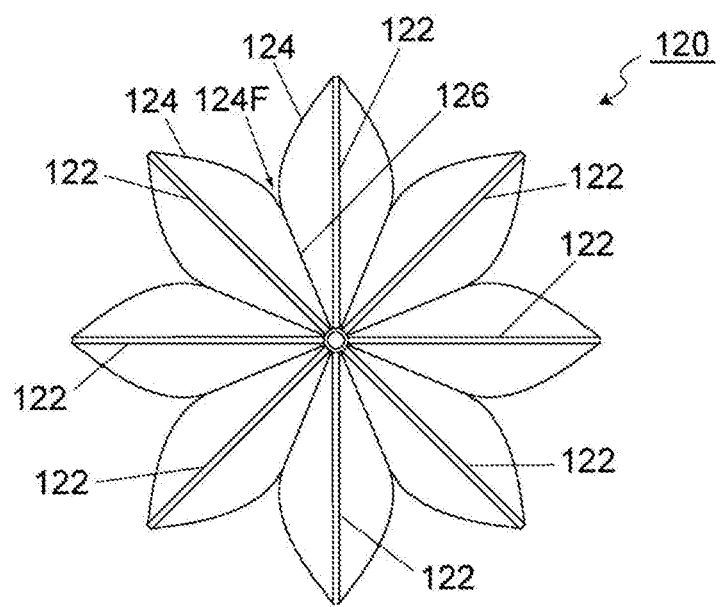
FIG. 5 is an enlarged left side view of a retriever.
Figure 6A:
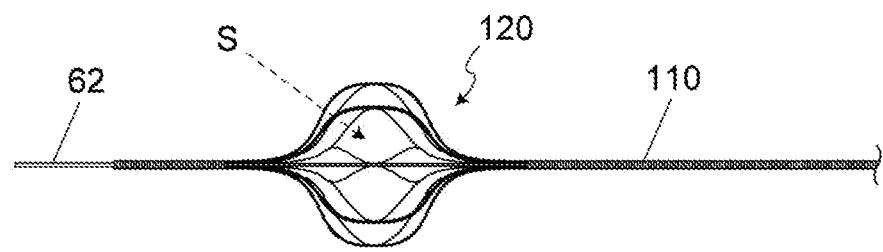
FIG. 6A is a diagram showing the retriever in a fully expanded state.
Figure 6B:
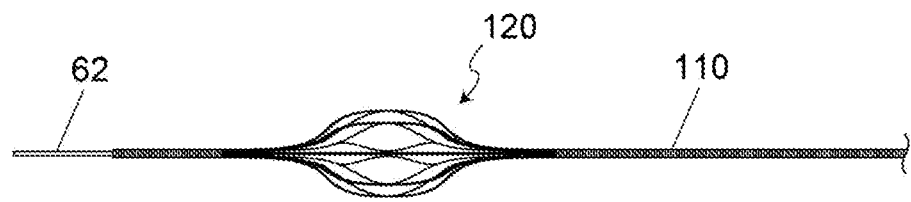
FIG. 6B is a diagram showing the retriever in a first semi-contracted state.
Figure 6C:
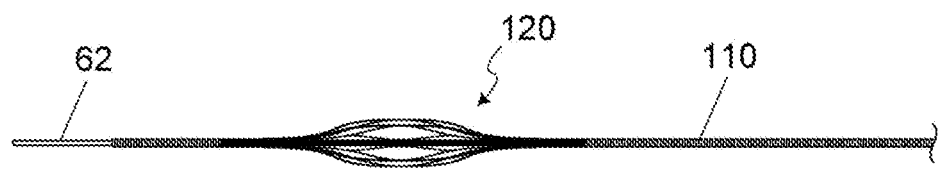
FIG. 6C is a diagram showing the retriever in a second semi-contracted state.
Figure 6D:
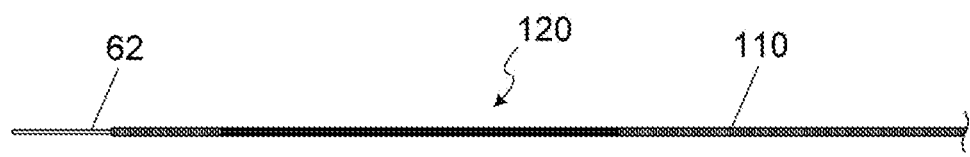
FIG. 6D is a diagram showing the retriever in a fully contracted state.

FIG. 3 is an enlarged perspective view of the foreign substance removing device 100 according to the first embodiment. FIGS. 4A and 4B are diagrams showing the retriever 120. FIG. 4A is an enlarged front view of the retriever 120, and FIG. 4B is a diagram showing an arrangement pattern of sub wires 124. To further describe FIG. 4B, two adjacent main wires 122, and sub wires 124 and regulating portions 126 which are disposed therebetween, are extracted from the retriever 120 shown in FIG. 4A, and the respective members are shown in a plan view. FIG. 5 is an enlarged left side view of the retriever 120. FIGS. 6A to 6D are diagrams showing how the retriever 120 expands and contracts. FIG. 6A shows a state in which the retriever 120 is most expanded, FIG. 6D shows a state in which the retriever 120 is most contracted, and FIGS. 6B and 6C show states during transition from an expanded state to a contracted state.

As shown in FIGS. 1 and 3, the foreign substance removing device 100 includes a tubular member 110, and the retriever 120 disposed at a distal portion of the tubular member 110.

The tubular member 110 is, for example, a pipe-shaped member having a circular cross section. As the material of the metal wire constituting the tubular member 110, for example, a known metal or metal alloy typified by stainless steel, titanium alloy, Ni—Ti alloy, Ni—Ti—Co alloy, Ni—Ti—Cu alloy, Au—Cd alloy, Cu—Al—Ni alloy, or the like may be preferably used. When a metal alloy having X-ray contrasting properties is used as the material of the elastic deformable portion, the elastic deformable portion may function as an X-ray impermeable marker. In this case, the position of the tubular member and the retriever can be identified from the outside of the body.

Notches (slits) extending in directions orthogonal to the tube axis are formed on an outer surface of the tubular member 110. As a result, flexibility of the tubular member 110 can be improved. As a method of forming the notches on the outer surface of the tubular member 110, for example, laser processing can be preferably used.

As shown in FIGS. 4A, 4B, and 5, the retriever 120 has the main wires 122 disposed to be centered around the tube axis of the tubular member 110, the sub wires 124 connecting the adjacent ones of the main wires 122 to each other, and the regulating portions 126 connected to the respective folding points 124F of the sub wires 124.

As shown in FIGS. 6A to 6D, the retriever 120 is configured to be expandable and contractible, and for example, the shape of the expanded state is memorized. The shape of the retriever 120 upon expansion is, for example, substantially spherical.

As is apparent from FIG. 5, the number of the main wires 122 constituting the retriever 120 is, for example, eight, and the main wires 122 are arranged at equal intervals centered around the tube axis of the tubular member 110 (at an arrangement interval of 45 degrees centered around the tube axis).

Each of the main wires 122 is configured to curve when the retriever 120 is expanded such that a space S having a predetermined size (see FIG. 6A) is provided by the eight main wires 122

As shown in FIGS. 4A and 4B, each of the plurality of sub wires 124 is configured to be foldable such that a pair of arm portions 124G, that extend away from each other from the folding point 124F toward the adjacent main wires 12, move toward each other (in other words, in a substantially V shape), and is arranged to be convex from an intermediate portion of the retriever 120 toward an end portion of the retriever 120.

Referring to FIG. 4B, when "first region A1" is defined as from the intermediate portion of the retriever 120 to a left end portion (an end portion on the distal side) of the retriever 120, and "second region A2" from the intermediate portion of the retriever 120 to a right end portion (an end portion on the proximal side) of the retriever, the sub wires 124 arranged in the first region A1 are arranged so as to be convex toward the left end portion of the retriever 120. On the other hand, the sub wires 124 arranged in the second region A2 are arranged so as to be convex toward the right end portion of the retriever 120. The sub wires 124 disposed in the first region A1 and the sub wires 124 disposed in the second region A2 are symmetrical with respect to the intermediate portion of the retriever 120.

In the present specification, the "intermediate portion of the retriever 120" refers to a region other than the end portions (the left end portion and the right end portion) of the retriever 120.

The regulating portions 126 connect the folding points 124F of the sub wires 124 and the end portions (the left end portion or the right end portion) of the retriever 120, respectively. As shown in FIG. 4B, the planar shape when the sub wires 124 and the regulating portions 126 are connected is substantially a Y shape.

As a material constituting the main wires 122, the sub wires 124, and the regulating portions 126, for example, a known metal or metal alloy typified by stainless steel, Ni—Ti alloy, titanium alloy, or the like may be preferably used. The main wires 122, the sub wires 124, and the regulating portions 126 are made from a material having super-elasticity (a reversible property of returning to its original shape from a deformed state as soon as the force is removed). As a material having super-elasticity, for example, Ni—Ti alloy may be suitably used.

Although not shown in the drawings, the tubular member 110 and the retriever 120 can be formed by to subjecting a single metal pipe (e.g., a pipe made of Ni—Ti alloy) to laser processing. In this case, the tubular member 110 and the retriever 120 can be formed integrally, and the main wires 122, the sub wires 124, and the regulating portions 126 constituting the retriever 120 can also be formed integrally.

Although not shown in the drawings, the cross-sectional shapes of the main wires 122, the sub wires 124, and the regulating portions 126 are substantially rectangular, for example. The main wires 122 have a larger cross-sectional area (are thicker wires) than the sub wires 124, and the main wires 122 have a rigidity higher than the sub wires 124.

Figure 7A:
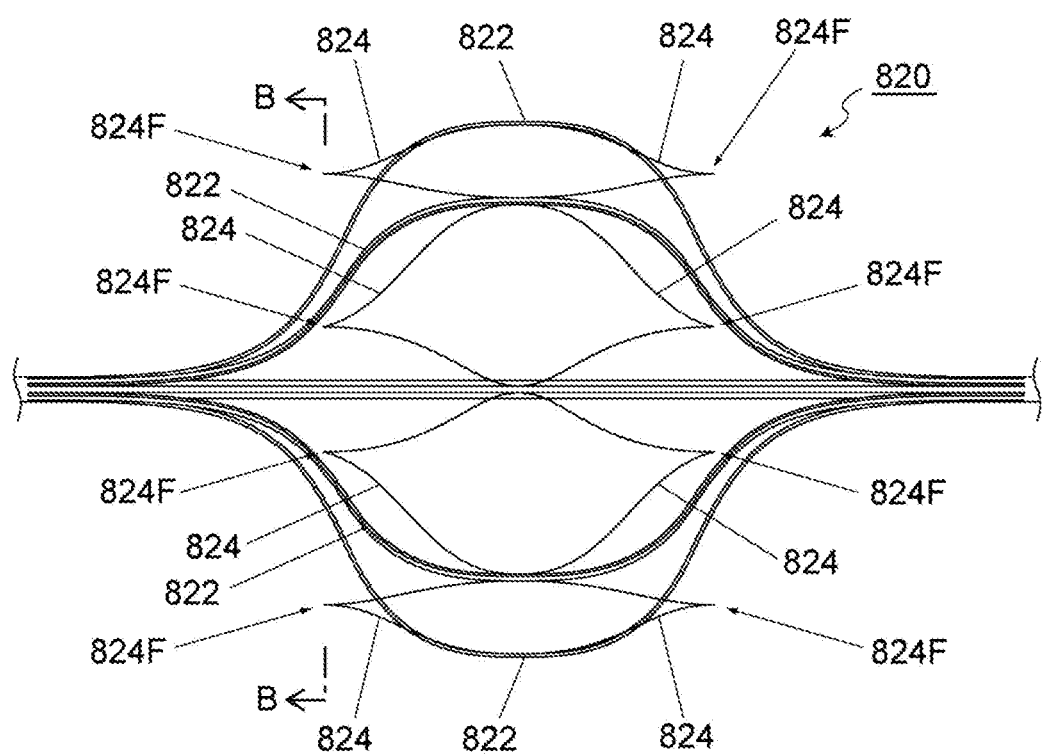
FIG. 7A is an enlarged front view of a retriever according to a comparative example.
Figure 7B:
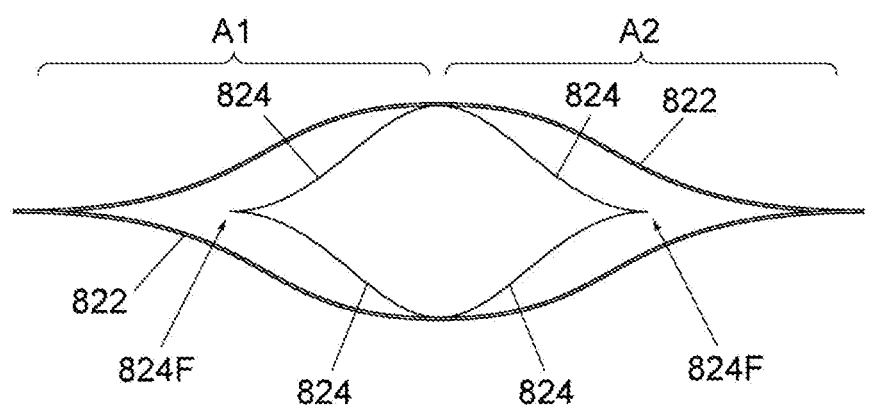
FIG. 7B is a diagram showing an arrangement pattern of sub wires in a retriever according to the comparative example.
Figure 8A:
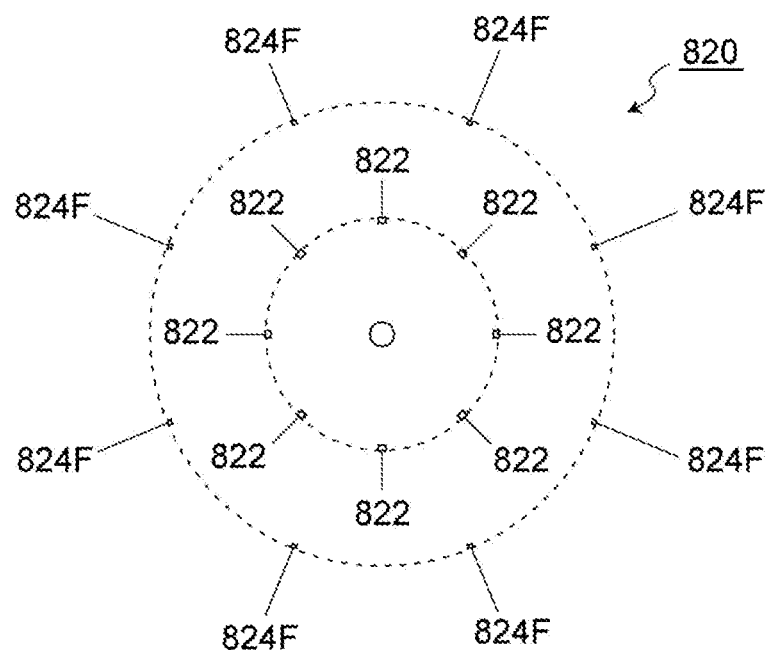
FIG. 8A is an end view taken along line B-B of FIG. 7A.
Figure 8B:
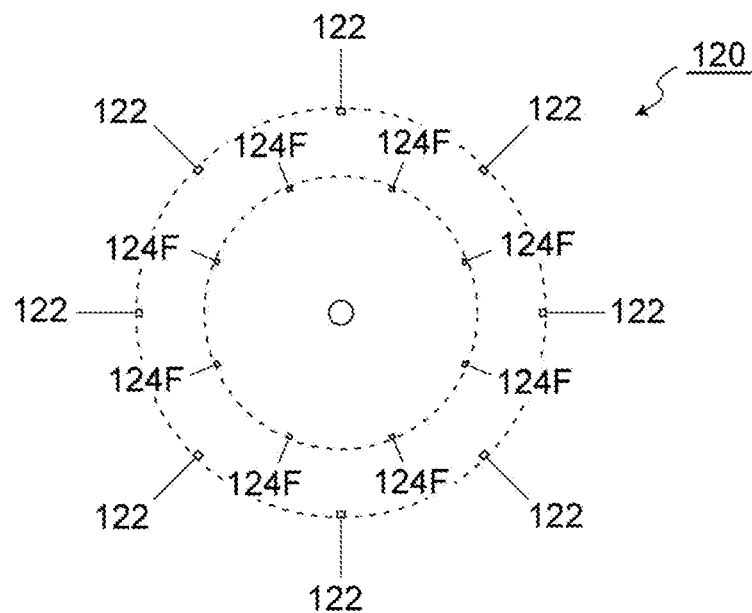
FIG. 8B is an end view taken along line A-A of FIG. 4B.

Here, the position of the folding points of the sub wires will be described in detail with reference to FIGS. 7 and 8. FIGS. 7A and 7B are diagrams showing a retriever 820 according to a comparative example. FIG. 7A is an enlarged front view of the retriever 820 according to the comparative example, and FIG. 7B is a diagram showing an arrangement pattern of sub wires 824 in the retriever 820 according to the comparative example. FIGS. 8A and 8B are diagrams showing the retrievers 820, 120 according to the comparative example and the first embodiment. FIG. 8A is an end view taken along line B-B of FIG. 7A, and is a diagram showing the positions of folding points 824F of the sub wires 824 with respect to the retriever 820 according to the comparative example. FIG. 8B is an end view taken along line A-A of FIG. 4A, and is a diagram showing the positions of the folding points 124F of the sub wires 124 with respect to the retriever 120 according to the first embodiment.

The retriever 820 according to the comparative example basically has the same configuration as the retriever 120 according to the first embodiment, but differs from the retriever 120 according to the first embodiment by not including the regulating portions as shown in FIGS. 7A and 7B. The folding points 824F of the sub wires 824 protrude out of the main wires 822 when the retriever 820 is expanded, and are not positioned inside the space formed by the eight main wires 822. In the retriever 820 according to the comparative example, as is apparent from FIG. 8A, the folding points 824F of the sub wires 824 are positioned outward of the main wires 822.

On the other hand, as shown in FIGS. 4A and 4B, the retriever 120 according to the first embodiment includes the regulating portions 126. The folding points 124F of the sub wires 124 are positioned inside the space S formed by the eight main wires 122 (see FIG. 6A) so that the sub wires 124 do not protrude out of the main wires 122 when the retriever is expanded. As is apparent from FIG. 8B, the folding points 124F of the sub wires 124 are positioned inward of the main wires 122.

Next, a method of using the foreign substance removing catheter 50 is described by referring to FIGS. 9A to 9F.

FIGS. 9A to 9F are diagrams showing the flow of using the foreign substance removing catheter 50 to remove foreign substance in a blood vessel. For the purpose of facilitating the understanding of the present invention, in FIGS. 9A to 9F, the shapes and the like of components of the foreign substance removing catheter 50 are shown schematically.

Figure 9A:
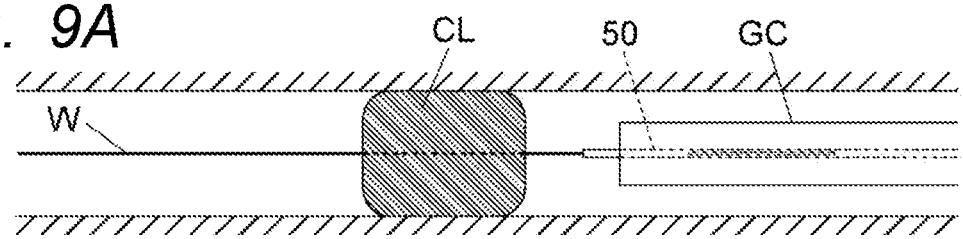
FIG. 9A is a diagram showing a method of using a foreign substance removing catheter in which the catheter is advanced to reach a position in front of a target site.

First, as shown in FIG. 9A, in a state where a guide wire W is inserted in the blood vessel, a guiding catheter GC is inserted into the blood vessel to be aligned with the guide wire W, and then the foreign substance removing catheter 50 is further advanced to reach a position right in front of a target site (a site where a foreign substance CL is present).

Figure 9B:
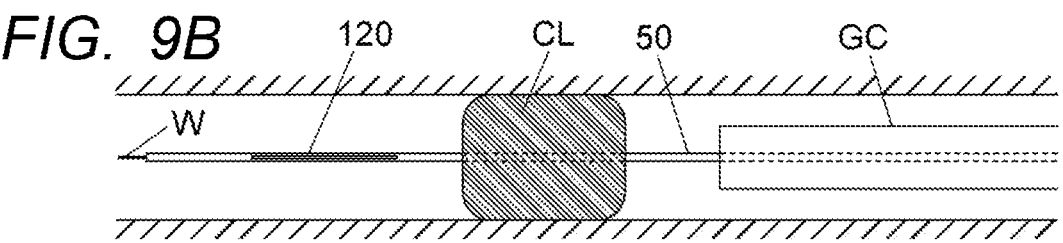
FIG. 9B is a diagram showing the method in which a retriever is disposed distal to the target site.

Next, as shown in FIG. 9B, the foreign substance removing catheter 50 is fed out from the guiding catheter GC, and is passed through the foreign substance CL in a state where the retriever 120 is contracted, and the retriever 120 is disposed distal to the target site.

Figure 9C:
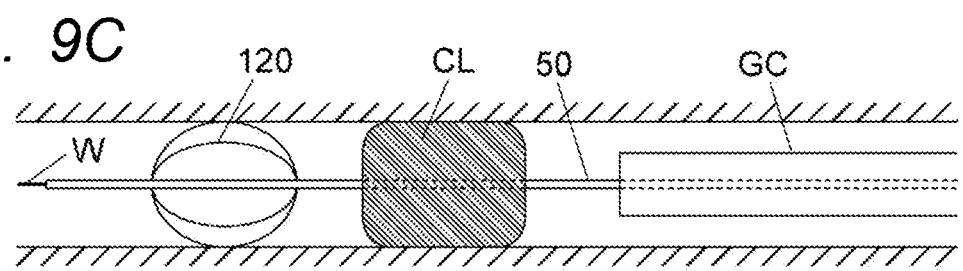
FIG. 9C is a diagram showing the method in which the retriever is expanded.
Figure 9D:
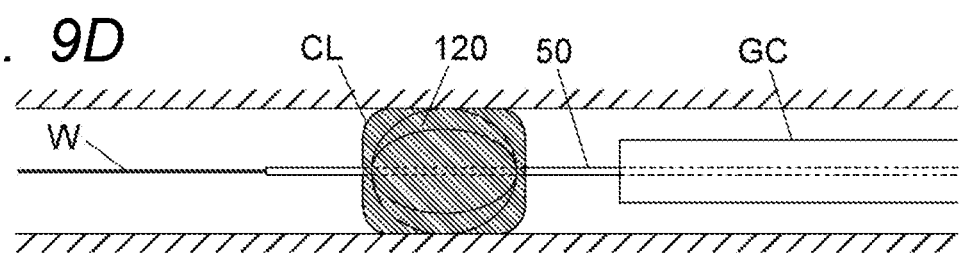
FIG. 9D is a diagram showing the method in which the foreign substance is entangled with the retriever.

Next, as shown in FIG. 9C, in a state where the retriever 120 is expanded, the foreign substance removing catheter 50 is retracted toward a side closer to the user, and the foreign substance CL in the blood vessel is entangled with the retriever 120 (see FIG. 9D). For example, the retriever 120 may be rotated around the tube axis at the target site, or may be moved forward and backward at the target site, or may be repeatedly expanded and contracted, so as to be entangled with the foreign substance CL.

Figure 9E:
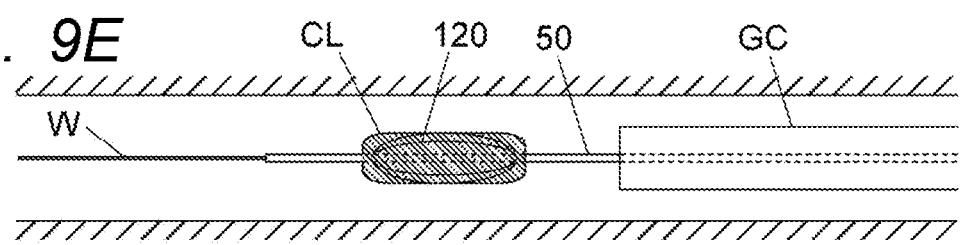
FIG. 9E is a diagram showing the method in which the retriever is contracted while being entangled with the foreign substance.
Figure 9F:
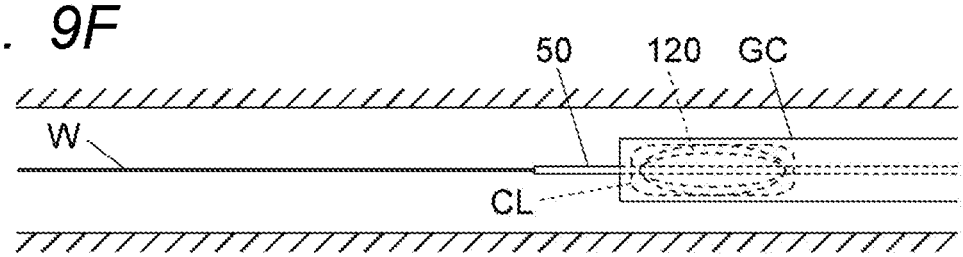
FIG. 9F is a diagram showing the method in which the retriever is drawn into a guiding catheter.

Then, as shown in FIG. 9E, the retriever 120 is contracted while being entangled with the foreign substance CL, and the retriever 120 (the foreign substance removing catheter 50) is drawn into the guiding catheter GC (see FIG. 9F). Thereafter, by extracting the foreign substance removing catheter 50 from the inside of the guiding catheter GC, the foreign substance CL can be taken out of the body percutaneously.

According to the foreign substance removing device 100 according to the first embodiment configured as described above, the eight main wires 122 are configured to provide the space S having a predetermined size when the retriever 120 is expanded, and the folding points 124F of the sub wires 124 are positioned inside the space S so that the sub wires 124 do not protrude out of the main wires 122 when the retriever 120 is expanded. Therefore, even if the retriever 120 is rotated in a state where the retriever 120 is expanded or the retriever 120 is moved forward or backward within the blood vessel, the folding points 124F of the sub wires 124 are unlikely to be caught in the blood vessel. As a result, it is possible to remove or collect foreign substance generated in the blood vessel while reducing a risk of damaging the blood vessel.

According to the foreign substance removing device 100 according to the first embodiment, since the plurality of regulating portions 126 are provided, the positions of the folding points 124F of the sub wires 124 can be kept inside the space S so that the sub wires 124 do not protrude out of the main wires 122 when the retriever 120 is expanded. As a result, the risk of damaging the blood vessel can be further reduced.

According to the foreign substance removing device 100 according to the first embodiment, each of the plurality of sub wires 124 is configured to be foldable such that the pair of arm portions 124G, that extend away from each other from the folding point 124F toward the adjacent main wires 122, move toward each other (in other words, in a substantially V shape), and the folding point 124F of the sub wire 124 and the end portions of the retriever 120 are connected by each of the plurality of regulating portions 126. Therefore, a foreign substance removing device capable of reducing the risk of damaging the blood vessel can be realized with a simple configuration.

According to the foreign substance removing device 100 according to the first embodiment, the plurality of sub wires 124 disposed in the first region A1 and in the second region A2 (see FIG. 4B) are symmetrical with respect to the intermediate portion of the retriever 120. Therefore, the retriever 120 can be expanded uniformly, and the foreign substance in the blood vessel can be removed or collected effectively.

When the rigidity of the main wires is extremely lower than the rigidity of the sub wires, it can be estimated that when the retriever is expanded, the main wires cannot be expanded as expected, or intervals between the adjacent main wires are not uniform. On the other hand, the foreign substance removing device 100 according to the first embodiment has a rigidity of the main wires 122 higher than the rigidity of the sub wires 124, and thus is an excellent thrombectomy device capable of easily expanding the main wires 122 as expected and maintaining a uniform interval between the adjacent main wires 122.

According to the foreign substance removing device 100 according to the first embodiment, since the shape of the retriever 120 upon expansion is substantially spherical, the expanded retriever 120 is further fitted to the blood vessel having a circular cross section. As a result, foreign substance sticking to an inner wall of the blood vessel can be removed effectively.

According to the foreign substance removing device 100 according to the first embodiment, each of the main wires 122, the sub wires 124, and the regulating portions 126 is made of a material having super-elasticity, and the shapes thereof in the expanded state are memorized. Therefore, the shape of the retriever 120 upon expansion can be stabilized.

The foreign substance removing catheter 50 according to the first embodiment includes the foreign substance removing device 100 described above, and thus is a foreign substance removing catheter capable of removing or collecting foreign substance generated in a blood vessel while reducing a risk of damaging the blood vessel.

Second Embodiment

Figure 10A:
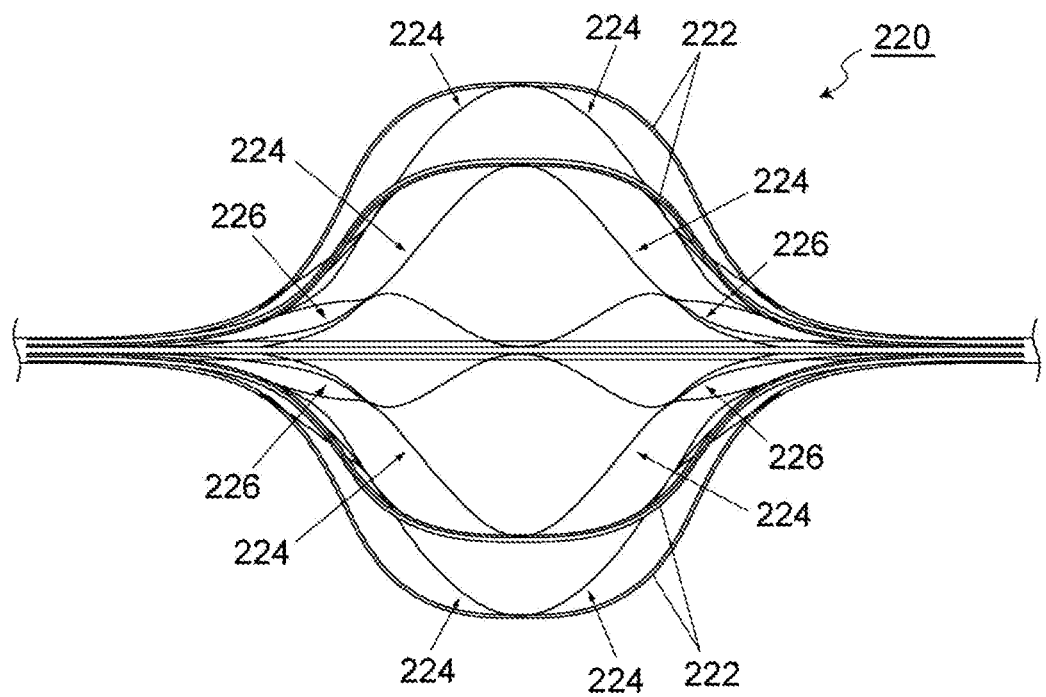
FIG. 10A is an enlarged front view of a retriever according to a second embodiment.
Figure 10B:
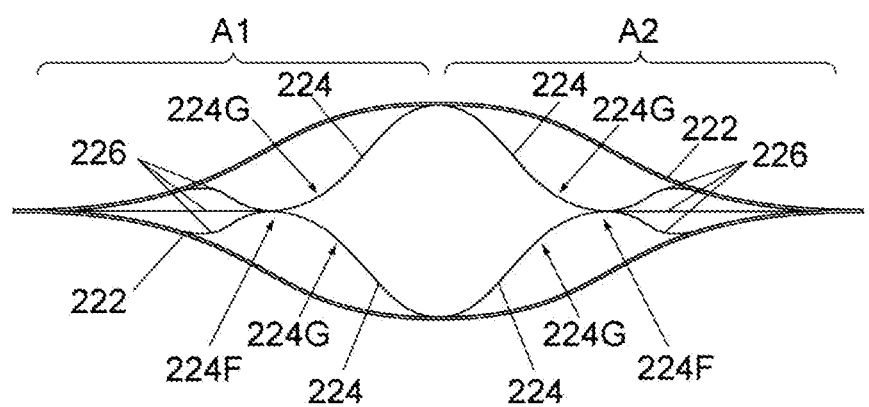
FIG. 10B is a diagram showing an arrangement pattern of sub wires in a retriever according to the second embodiment.

FIGS. 10A and 10B are diagrams showing a retrievers 220 according to a second embodiment. FIG. 10A is an enlarged front view of the retriever 220, and FIG. 10B is a diagram showing an arrangement pattern of sub wires 224 in the retriever 220. To further describe FIG. 10B, two adjacent main wires 222, and sub wires 224 and regulating portions 226 which are disposed therebetween, are extracted from the retriever 220 shown in FIG. 10A, and the respective members are shown in a plan view.

The foreign substance removing device according to the second embodiment basically has the same construction as the foreign substance removing device 100 according to the first embodiment, but the configuration of the retriever differs from that of the foreign substance removing device 100 according to the first embodiment.

As shown in FIGS. 10A and 10B, the retriever 220 according to the second embodiment has eight main wires 222, the sub wires 224 connecting adjacent ones of the main wires 222 to each other, and the regulating portions 226 connected to the respective folding points 224F of the sub wires 224. A pair of arm portions 224G extend away from each other from each of the folding points 224F toward the adjacent main wires 222.

Since the configuration of the main wires 222 and the sub wires 224 is the same as the main wires 122 and the sub wires 124 described in the first embodiment, a specific description thereof will be omitted.

The regulating portions 226 connect the folding points 224F of the sub wires 224 and the end portions (the left end portion or the right end portion) of the retriever 220, respectively. As compared with the regulating portions 126 described in the first embodiment, one regulating portion 126 of the first embodiment is disposed in each of the first region A1 and the second region A2, as shown in FIG. 4B, whereas three regulating portions 226 of the second embodiment are disposed in each of the first region A1 and the second region A2, as shown in FIG. 10B.

Since the material of the main wires 222, the sub wires 224, and the regulating portions 226 are identical to that of the main wires 122, the sub wires 124, and the regulating portions 126 described in the first embodiment, a specific description thereof will be omitted.

Since the configuration of the foreign substance removing device according to the components of the second embodiment other than the retriever 220 (e.g., the tubular member and the like) is the same as those described in the first embodiment, a specific description thereof will be omitted.

As described above, although the foreign substance removing device according to the second embodiment is different from the foreign substance removing device 100 according to the first embodiment in that the configuration of the retriever (the number of regulating portions) is different, but similar as the foreign substance removing device 100 according to the first embodiment, the eight main wires 222 are configured to provide a space having a predetermined size when the retriever 220 is expanded, and the folding points 224F of the sub wires 224 are positioned inside the space so that the sub wires 224 do not protrude out of the main wires 222 when the retriever 220 is expanded. Therefore, even if the retriever 220 is rotated in a state where the retriever 220 is expanded or the retriever 220 is moved forward or backward within the blood vessel, the folding points 224F of the sub wires 224 are unlikely to be caught in the blood vessel. As a result, it is possible to remove or collect foreign substance generated in the blood vessel while reducing a risk of damaging the blood vessel.

In the foreign substance removing device according to the second embodiment, as shown in FIG. 10B, three regulating portions 226 are disposed in each of the first region A1 and the second region A2. Therefore, a force that keeps the positions of the folding points 224F of the sub wires 224 in the space can be further increased. As a result, the risk of damaging the tubular tissue can be further reduced.

The foreign substance removing device according to the second embodiment has the same configuration as the foreign substance removing device 100 according to the first embodiment except for the configuration of the retriever (the number of the regulating portions), and thus has the corresponding effects among the effects of the foreign substance removing device 100 according to the first embodiment.

Third Embodiment

Figure 11:
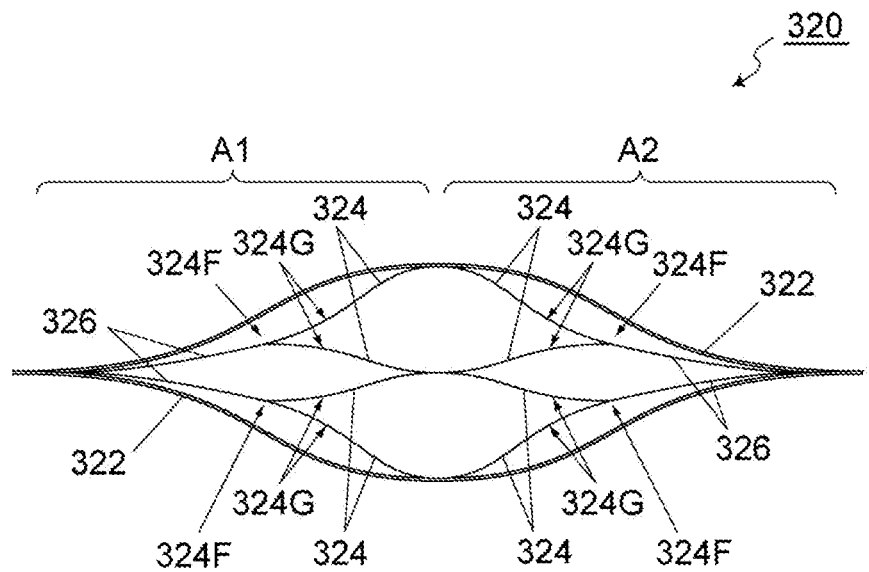
FIG. 11 is a diagram showing an arrangement pattern of sub wires in a retriever according to a third embodiment.

FIG. 11 is a diagram showing an arrangement pattern of sub wires 324 in a retriever 320 according to a third embodiment. In FIG. 11, two adjacent main wires 322, and sub wires 324 and regulating portions 326 which are disposed therebetween, are extracted from the entire retriever 320, and the respective members are shown in a plan view.

The foreign substance removing device according to the third embodiment basically has the same construction as the foreign substance removing device 100 according to the first embodiment, but the configuration of the retriever differs from that of the foreign substance removing device 100 according to the first embodiment.

As shown in FIG. 11, the retriever 320 according to the third embodiment has the main wires 322, the sub wires 324 connecting adjacent ones of the main wires 322 to each other, and the regulating portions 326 connected to the respective folding points 324F of the sub wires 324.

Since the configuration of the main wires 322 is the same as the main wires 122 described in the first embodiment, a specific description thereof will be omitted. Although not shown in the drawings, similar as the retriever 120 described in the first embodiment, the number of the main wires 322 constituting the retriever 320 is eight, and the main wires 322 are arranged at equal intervals centered around the tube axis of the tubular member (at an arrangement interval of 45 degrees centered around the tube axis).

As shown in FIG. 11, each of the plurality of sub wires 324 is configured to be foldable at two points (foldable in a substantially W shape) between the adjacent main wires 322, and is arranged to be convex from an intermediate portion of the retriever 320 toward an end portion of the retriever 320. The sub wires 324 disposed in the first region A1 and the sub wires 324 disposed in the second region A2 are symmetrical with respect to the intermediate portion of the retriever 320. A pair of arm portions 324G extend away from each other respectively from the two folding points 324F toward the adjacent main wires 322. More specifically, one arm portions 324G extending from one folding points 324F (on the upper side in the drawing) is connected to the main wire 322 on the upper side in the drawing, and the other arm portions 324G extending from the other folding points 324F (on the lower side in the drawing) is connected to the main wire 322 on the lower side in the drawing. Further, the other arm portions 324G extending from the one of the folding points 324F (on the upper side in the drawing) and the one arm portions 324G extending from the other folding points 324F (on the lower side in the drawing) are connected to each other.

The regulating portions 326 connect the folding points 324F of the sub wires 324 and the end portions (the left end portion or the right end portion) of the retriever 320, respectively. As compared with the regulating portions 126 described in the first embodiment, one regulating portion 126 of the first embodiment is disposed in each of the first region A1 and the second region A2, as shown in FIG. 4B, whereas two regulating portions 326 of the third embodiment are disposed in each of the first region A1 and the second region A2, as shown in FIG. 11.

Since the material of the main wires 322, the sub wires 324, and the regulating portions 326 are identical to that of the main wires 122, the sub wires 124, and the regulating portions 126 described in the first embodiment, a specific description thereof will be omitted.

Since the configuration of the foreign substance removing device according to the components of the third embodiment other than the retriever 320 (e.g., the tubular member and the like) is the same as those described in the first embodiment, a specific description thereof will be omitted.

As described above, although the foreign substance removing device according to the third embodiment is different from the foreign substance removing device 100 according to the first embodiment in that the configuration of the retriever (the configuration of the sub wires and the regulating portions) is different, but similar as the foreign substance removing device 100 according to the first embodiment, the eight main wires 322 are configured to provide a space having a predetermined size when the retriever 320 is expanded, and the folding points 324F of the sub wires 324 are positioned inside the space so that the sub wires 324 do not protrude out of the main wires 322 when the retriever 320 is expanded. Therefore, even if the retriever 320 is rotated in a state where the retriever 320 is expanded or the retriever 320 is moved forward or backward within the blood vessel, the folding points 324F of the sub wires 324 are unlikely to be caught in the blood vessel. As a result, it is possible to remove or collect foreign substance generated in the blood vessel while reducing a risk of damaging the blood vessel.

The foreign substance removing device according to the third embodiment has the same configuration as the foreign substance removing device 100 according to the first embodiment except for the configuration of the retriever (the configuration of the sub wires and the regulating portions), and thus has the corresponding effects among the effects of the foreign substance removing device 100 according to the first embodiment.

Fourth Embodiment

Figure 12:
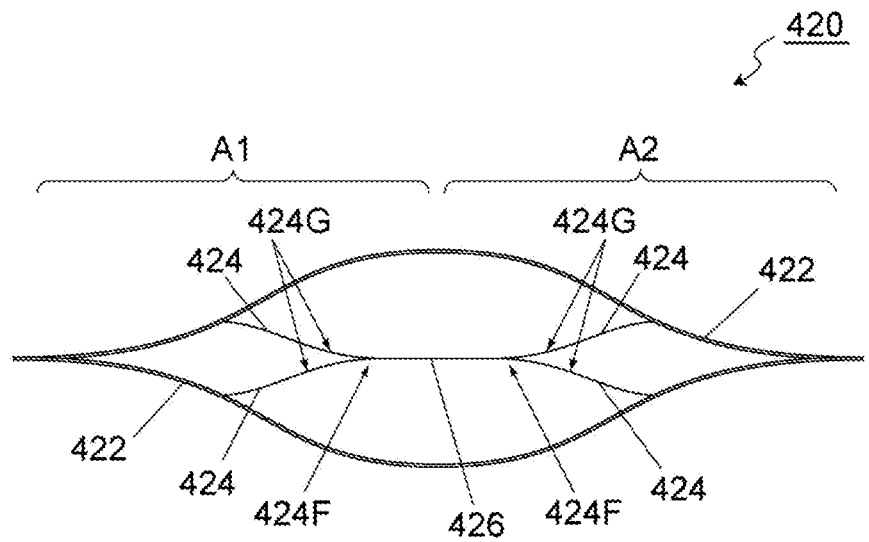
FIG. 12 is a diagram showing an arrangement pattern of sub wires in a retriever according to a fourth embodiment.

FIG. 12 is a diagram showing an arrangement pattern of sub wires 424 in a retriever 420 according to a fourth embodiment. In FIG. 12, two adjacent main wires 422, and sub wires 424 and a regulating portion 426 which are disposed therebetween, are extracted from the entire retriever 420, and the respective members are shown in a plan view.

The foreign substance removing device according to the fourth embodiment basically has the same construction as the foreign substance removing device 100 according to the first embodiment, but the configuration of the retriever differs from that of the foreign substance removing device 100 according to the first embodiment.

As shown in FIG. 12, the retriever 420 according to the fourth embodiment has the main wires 422, the sub wires 424 connecting adjacent ones of the main wires 422 to each other, and the regulating portions 426 respectively connected to folding points 424F of the sub wires 424. A pair of arm portions 424G extend away from each other from each of the folding points 424F toward the adjacent main wires 422.

Since the configuration of the main wires 422 is the same as the main wires 122 described in the first embodiment, a specific description thereof will be omitted. Although not shown in the drawings, similar as the retriever 120 described in the first embodiment, the number of the main wires 422 constituting the retriever 420 is eight, and the main wires 422 are arranged at equal intervals centered around the tube axis of the tubular member (at an arrangement interval of 45 degrees centered around the tube axis).

As shown in FIG. 12, each of the plurality of sub wires 424 is configured to be foldable such that a pair of arm portions 424G move toward each other (in other words, in a substantially V shape), and is arranged to be convex from an end portion of the retriever 420 toward an intermediate portion of the retriever 420. The sub wires 424 disposed in the first region A1 and the sub wires 424 disposed in the second region A2 are symmetrical with respect to the intermediate portion of the retriever 420. Comparing the sub wires 124 described in the first embodiment with the sub wires 424 of the fourth embodiment, the sub wires 424 of the fourth embodiment have an opposite arrangement orientation.

The regulating portion 426 connects the folding points 424F of the sub wires 424 to each other. As compared with the regulating portions 126 described in the first embodiment, one regulating portion 126 of the first embodiment is disposed in each of the first region A1 and the second region A2, as shown in FIG. 4B, whereas one regulating portions 426 of the fourth embodiment is disposed spanning from the first region A1 to the second region A2, as shown in FIG. 12.

Since the material of the main wires 422, the sub wires 424, and the regulating portions 426 are identical to that of the main wires 122, the sub wires 124, and the regulating portions 126 described in the first embodiment, a specific description thereof will be omitted.

Since the configuration of the foreign substance removing device according to the components of the fourth embodiment other than the retriever 420 (e.g., the tubular member and the like) is the same as those described in the first embodiment, a specific description thereof will be omitted.

As described above, although the foreign substance removing device according to the fourth embodiment is different from the foreign substance removing device 100 according to the first embodiment in that the configuration of the retriever (the configuration of the sub wires and the regulating portions) is different, but similar as the foreign substance removing device 100 according to the first embodiment, the eight main wires 422 are configured to provide a space having a predetermined size when the retriever 420 is expanded, and the folding points 424F of the sub wires 424 are positioned inside the space so that the sub wires 424 do not protrude out of the main wires 422 when the retriever 420 is expanded. Therefore, even if the retriever 420 is rotated in a state where the retriever 420 is expanded or the retriever 420 is moved forward or backward within the blood vessel, the folding points 424F of the sub wires 424 are unlikely to be caught in the blood vessel. As a result, it is possible to remove or collect foreign substance generated in the blood vessel while reducing a risk of damaging the blood vessel.

The foreign substance removing device according to the fourth embodiment has the same configuration as the foreign substance removing device 100 according to the first embodiment except for the configuration of the retriever (the configuration of the sub wires and the regulating portions), and thus has the corresponding effects among the effects of the foreign substance removing device 100 according to the first embodiment.

Fifth Embodiment

In a fifth embodiment, as an example of the foreign substance collecting system of the present invention, a thrombus collecting system that removes foreign substance such as a thrombus or an embolus generated in a blood vessel will be described as an example.

Figure 13:
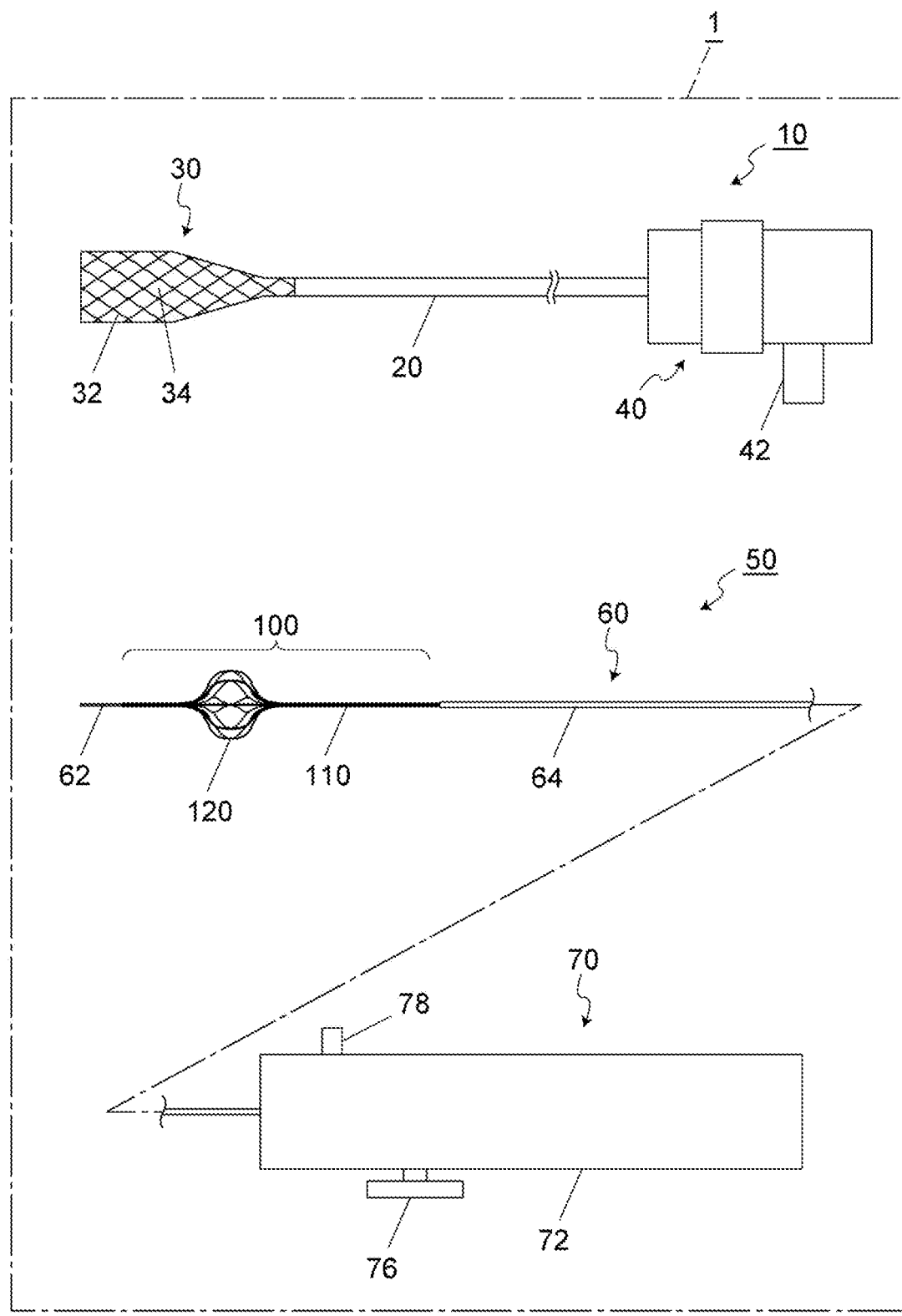
FIG. 13 is a diagram showing a foreign substance collecting system according to a fifth embodiment.

FIG. 13 is a diagram showing a foreign substance collecting system 1 according to the fifth embodiment. FIGS.

14A to 14F are diagrams showing a method of using the foreign substance collecting system 1.

As shown in FIG. 13, the foreign substance collecting system 1 according to the fifth embodiment includes: the foreign substance that removes catheter 50 for removing a foreign substance in a blood vessel; and a foreign substance capturing catheter 10 that captures foreign substance in the blood vessel.

Since the foreign substance removing catheter 50 as shown in FIG. 13 is the same as the foreign substance removing catheter 50 described in the first embodiment, a specific description thereof will be omitted.

The foreign substance capturing catheter 10 includes a catheter tube 20, a capture 30 disposed at a distal portion of the catheter tube 20, and a base 40 disposed at a proximal portion of the catheter tube 20. The foreign substance capturing catheter 10 is a thrombus that captures catheter for capturing foreign substance, such as a thrombus or an embolus generated in a blood vessel.

Although not shown in the drawings, the catheter tube 20 and the base 40 have a lumen provided therein to allow the foreign substance removing catheter 50 to pass through.

The material of the catheter tube 20 is the same as that of the first rube 62 and the second tube 64 in the foreign substance removing catheter 50. Therefore, a detailed description thereof will be omitted.

The capture 30 includes a substantially cylindrical mesh portion 32 and a membrane portion 34 formed to surround the entire mesh portion 32.

A proximal portion of the mesh portion 32 has a tapered shape that gradually increases in diameter from a proximal side (a side closer to the user) toward a distal side (a tip end side). A tip end portion of the mesh portion 32 is configured to open when the capture 30 is expanded.

The mesh portion 32 is formed by, for example, by weaving thin metal wires into a lattice shape. As the material of the thin metal wires used for the mesh portion 32, for example, a known metal or metal alloy typified by stainless steel, Ni—Ti alloy, titanium alloy, or the like may be preferably used. The mesh portion 32 is made from a material having super-elasticity. As a material having super-elasticity, for example, Ni—Ti alloy may be suitably used. As will be described in detail later, the mesh portion 32 is configured to be expandable and contractible in a radial direction (a direction orthogonal to the tube axis), and for example, the shape of the expanded state is memorized.

Preferably, the membrane portion 34 may be made of, for example, fluoro-resin such as polytetrafluoroethylene (PTFE), polyurethane resin, etc. A membrane-shaped member made of the resin material has good biocompatibility and durability and may be chemically stable.

A port 42 in communication with an internal lumen is provided on a side surface of the base 40, and is configured such that a liquid such as saline, for example, can be charged into in the catheter tube 20 via the port 42. Although not shown in the drawings, an opening end portion of the port 42 can be closed in a liquid-tight manner by a closing member such as a cap or a valve made of a silicon rubber or the like.

Next, a method of using the foreign substance collecting system 1 is described by referring to FIGS. 14A to 14F.

FIGS. 14A to 14F are diagrams showing the flow of using the foreign substance collecting system 1 to remove foreign substance in a blood vessel. For the purpose of facilitating the understanding of the present invention, in FIGS. 14A to 14F, the shapes and the like of components of the foreign substance collecting system 1 are shown schematically.

Figure 14A:
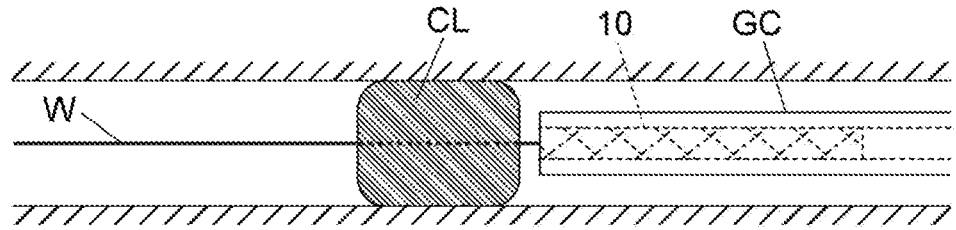
FIG. 14A is a diagram showing a method of using a foreign substance collecting system in which in which a foreign substance collecting catheter is advanced to reach a position in front of a target site.

First, as shown in FIG. 14A, in a state where a guide wire W is inserted in the blood vessel, a guiding catheter GC is inserted into the blood vessel to be aligned with the guide wire W, and then the foreign substance capturing catheter 10 is further advanced to reach a position right in front of a target site (a site where a foreign substance CL is present).

Figure 14B:
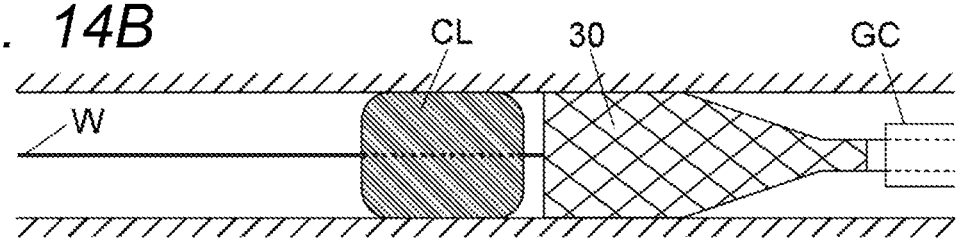
FIG. 14B is a diagram showing the method in which a guiding catheter GC is retracted toward a side closer to the user and a capture 30 is exposed from the guiding catheter.

Next, as shown in FIG. 14B, in a state where the position of the foreign substance capturing catheter 10 is fixed, the guiding catheter GC is retracted toward a side closer to the user, and the capture 30 is exposed from the guiding catheter GC. Thereby, the capture 30 is expanded to be in close contact with the blood vessel wall.

Figure 14C:
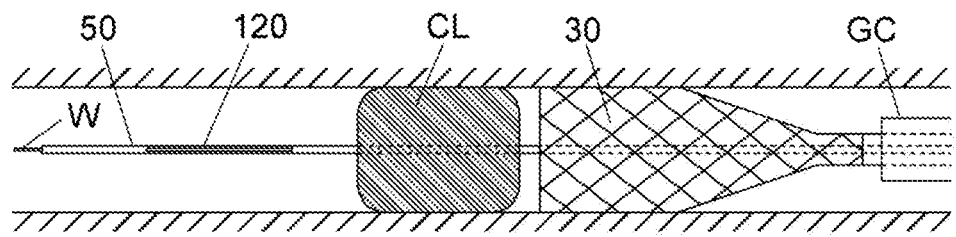
FIG. 14C is a diagram showing the method in which the foreign substance capturing catheter is passed through a foreign substance in a state where a retriever is contracted.
Figure 14D:
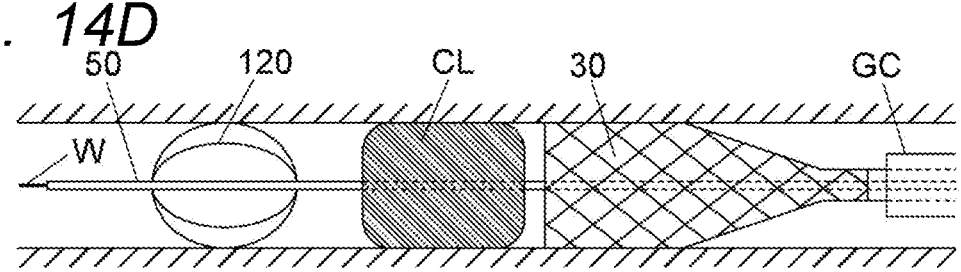
FIG. 14D is a diagram showing the method in which the foreign substance is entangled with the retriever.

Next, as shown in FIG. 14C, the foreign substance removing catheter 50 is fed out via the internal lumen of the foreign substance capturing catheter 10, and is passed through the foreign substance CL in a state where the retriever 120 is contracted, and the retriever 120 is disposed distal to the target site.

Figure 14E:
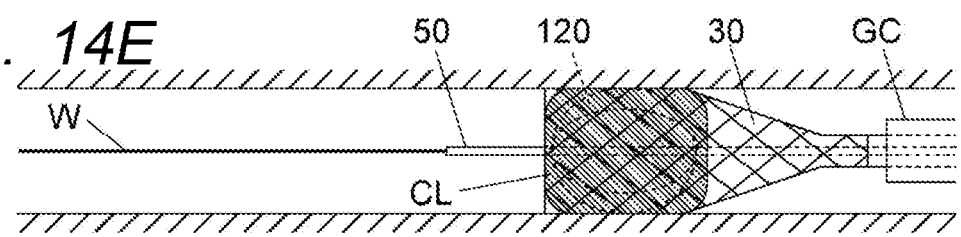
FIG. 14E is a diagram showing the method in which the foreign substance removing catheter is retracted toward the side closer to the user, and the foreign substance is taken into the capture.

Next, in a state where the retriever 120 is expanded (see FIG. 14D), the foreign substance removing catheter 50 is retracted toward the side closer to the user, and the foreign substance CL is taken into the capture 30 (see FIG. 14E).

Figure 14F:
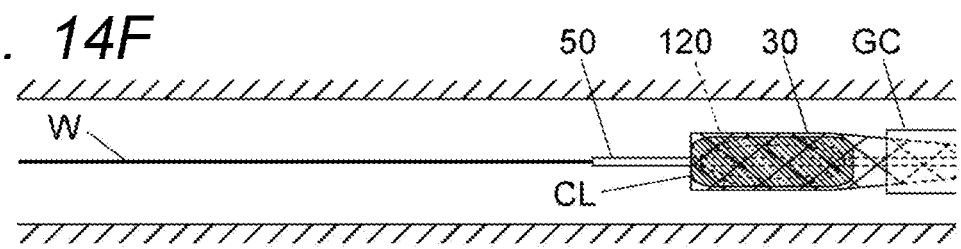
FIG. 14F is a diagram showing the method in which the foreign substance is taken into the capture and the capture is drawn into the guiding catheter.
Figure 15:
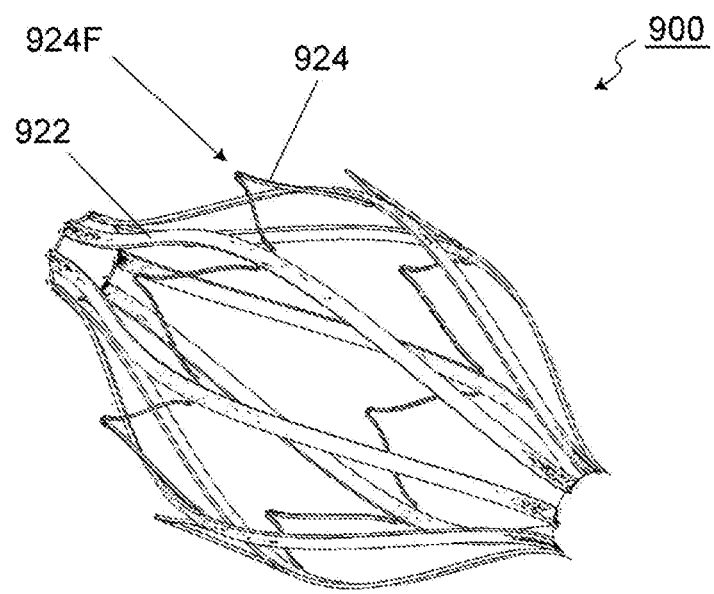
FIG. 15 is an enlarged perspective view of a thrombectomy device of related art.

Then, in a state where the foreign substance CL is taken into the capture 30, the capture 30 is drawn into the guiding catheter GC (see FIG. 14F). Thereafter, by extracting the foreign substance capturing catheter 10 from the inside of the guiding catheter GC, the foreign substance CL can be taken out of the body percutaneously.

The foreign substance collecting system 1 according to the fifth embodiment includes the foreign substance removing catheter 50 described above, and thus is a foreign substance collecting system capable of removing or collecting foreign substance generated in a blood vessel while reducing a risk of damaging the blood vessel.

While the present invention has been described with reference to certain exemplary embodiments thereof, it will be understood by those skilled in the art that various changes and modifications may be made therein. For example, the following modifications are possible.

(1) In the embodiments described above, a case where each of the plurality of sub wires is configured to be foldable at one or two points between the adjacent main wires has been described as an example, but the present invention is not limited thereto. Each of the plurality of sub wires may be configured to be foldable at three or more points between the adjacent main wires. In a case where each of the plurality of sub wires is configured to be foldable at three or more points between the adjacent main wires, the number of the regulating portions may be changed in accordance with the number of folding points of the sub wires. In the above embodiment, a case where the regulating portions are provided to regulate the positions of the folding points in the sub wires has been described as an example, but the present invention is not limited thereto. The folding points of the sub wires may be configured so that the sub wires do not protrude out of the plurality of main wires when the retriever is expanded by, for example, previously providing creases to the sub wires without providing the regulating portions.

(2) In the embodiments described above, a case where the sub wires disposed in the first region and the sub wires disposed in the second region are symmetrical with respect to the intermediate portion of the retriever has been described as an example, but the present invention is not limited thereto. The sub wires disposed in the first region and the sub wires disposed in the second region may be asymmetrical with respect to the intermediate portion of the retriever.

(3) In the embodiments described above, a case where the shape of the retriever upon expansion is substantially spherical has been described as an example, but the present invention is not limited thereto. For example, the shape may be spherical, prolate, oblate, or egg shaped. In another example, the respective end portions of the retriever may have prolate shapes and the intermediate portion of the retriever may be cylindrical.

(4) In the embodiments described above, a case where the cross-sectional shape of the tubular member is circular has been described as an example, but the present invention is not limited thereto. For example, the shape may be elliptical or polygonal.

(5) In the embodiments described above, a case where the tubular member and the retriever are formed integrally has been described as an example, but the present invention is not limited thereto. For example, the tubular member and the retriever may be formed separately, and then joined to each other via adhesion, welding, or the like. Regarding the main wires, the sub wires, and the regulating portions constituting the retriever, similarly, for example, the main wires and the sub wires may be integrally formed by laser processing, and the regulating portion may be formed separately, and then bonded to the main wires and the sub wires via adhesion, welding, or the like.

(6) In the embodiments described above, a case where the shape of the retriever in the expanded state is memorized has been described as an example, but the present invention is not limited thereto. For example, the shape of the contracted state as shown in FIG. 6D may be memorized, or the shape of the semi-expanded state shown in FIGS. 6B and 6C may be memorized.

(7) In the embodiments described above, a case where the number of the main wires constituting the retriever is eight has been described as an example, but the present invention is not limited thereto. For example, the number may be seven or less or nine or more. Further, in the embodiments described above, a case where the main wires are arranged at equal intervals centered around the tube axis of the tubular member (so that the angles formed between the adjacent main wires are equal) has been described as an example, but the present invention is not limited thereto. For example, the main wires may be arranged such that the angle formed between the adjacent main wires is not uniform.

(8) In the embodiments described above, a case where the cross-sectional shapes of the main wires, the sub wires, and the regulating portions are substantially rectangular has been described as an example, but the present invention is not limited thereto. For example, the shapes may be circular or elliptical, or a polygonal shape other than quadrangular.

(9) In the embodiments described above, a case where the main wires, the sub wires, and the regulating portions (and the tubular member) are made of a metal material has been described as an example, but the present invention is not limited thereto. For example, the material may be a biocompatible resin or the like.

(10) In the embodiments described above, a case where the end portion on the proximal side of the foreign substance removing device is connected to the inner peripheral surface of the distal portion of the second tube has been described as an example, but the present invention is not limited thereto. For example, the end portion on the proximal side of the foreign substance removing device may be connected to the outer peripheral surface of the distal portion of the second tube.

(11) In the first embodiment described above, as the structure of the foreign substance removing catheter, a case where the retriever 120 contracts when the slider 76 is moved in the X1 direction shown in FIG. 2A and expands when the slider 76 is moved in the X2 direction shown in FIG. 2B has been described as an example, but the present invention is not limited thereto. For example, by providing a gear mechanism or the like inside the operation portion, it is possible to provide a structure in which the retriever expands when the slider is moved in the X1 direction shown in FIG. 2A and in which the retriever contracts when the slider is moved in the X2 direction shown in FIG. 2B.

(12) In the first embodiment described above, a case where expansion and contraction of the retriever is operated by operating the slider that moves in parallel along the tube axis direction has been described as an example, but the present invention is not limited thereto. For example, a member corresponding to the slider may be configured to move in the circumferential direction centered around the tube axis, and expansion and contraction of the retriever may be operated by moving the member in the circumferential direction. Alternatively, instead of the slider, extension and contraction of the retriever may be operated via lever operation, button operation, or the like. Further, a sheath may be placed on the outer periphery of the retriever in the contracted state so as to move the sheath in the axial direction in a state where the position of the retriever is fixed. In this case, when the retriever is exposed from the sheath, the retriever expands, and when the retriever is housed in the sheath, the retriever contracts.

(13) In each of the first to fifth embodiments described above, the operation portion is configured such that the states in which the retriever is contracted and the expanded state can be changed in both directions (that is, both change from the contracted state to the expanded state and change from the expanded state to the contracted state are possible). However, for example, the operation portion may be configured such that only change in one direction (that is, change from the contracted state to the expanded state, or change from the expanded state to the contracted state) is possible, and change in the other direction may be realized by elasticity of the retriever itself or the like. In other words, the phrase "operating expansion and contraction of the retriever" indicates realizing switching between the expanded state and the contracted state of the retriever, and is inclusive of not only switching between the states in both directions, but also switching to either state in only one direction.

(14) In the fifth embodiment described above, a case where the membrane portion is formed to surround the entire mesh portion in the capture has been described as an example, but the present invention is not limited thereto. For example, a tapered portion of the mesh portion (a proximal portion of the mesh portion) may be exposed without being covered by the membrane portion. The material of the mesh portion is not limited to metal, and may be a biocompatible resin or the like.

(15) In the embodiments described above, a case where the tubular tissue as a target of use is a blood vessel has been described as an example, but the present invention is not limited thereto. The present invention is applicable to a foreign substance removing device, a foreign substance removing catheter, and a foreign substance collecting system that removes or collects foreign substance generated inside other tubular tissues such as a gastrointestinal tract and a bile duct.

This application is based on Japanese Patent Application No. 2017-022993 filed Feb. 10, 2017, the content of which is incorporated herein by reference.

INDUSTRIAL APPLICABILITY

According to the foreign substance removing device, the foreign substance removing catheter, and the foreign substance collecting system of the present invention, it is possible to remove or collect foreign substance generated in a tubular tissue while reducing the risk of damaging the tubular tissue. The present invention having this effect is useful for a foreign substance removing device, a foreign substance removing catheter, and a foreign substance collecting system.

DESCRIPTION OF REFERENCE SIGNS

1 Foreign substance collecting system
10 Foreign substance capturing catheter
20 Catheter tube
30 Capture
32 Mesh portion
34 Membrane portion
40 Base
42 Port
50 Foreign substance removing catheter
60 Catheter body
62 First tube
64 Second tube
70 Operation portion
72 Operation body
74 Slot
76 Slider
78 Liquid injection port
100 Foreign substance removing device
110 Tubular member
120, 220, 320, 420, 820 Retriever
122, 222, 322, 422, 822 Main wire
124, 224, 324, 424, 824 Sub wire
124F, 224F, 324F, 424F, 824F Folding point (of sub wire)
124G, 224G, 324G, 424G Arm portion (of sub wire)
126, 226, 326, 426 Regulating portion
900 Thrombectomy device
922 Cage
924 Flat wire
924F Folding point (of flat wire)
A1 First region
A2 Second region
CL Foreign substance
GC Guiding catheter
S Space (in retriever)
W Guide wire

The invention claimed is:

1. A foreign substance removing device for removing a foreign substance in a body lumen, the foreign substance removing device comprising:
a tubular member; and
a retriever disposed in a portion of the tubular member and configured to be expandable to and contractible from a predetermined shape,
wherein the retriever comprises:
a plurality of main wires disposed to be centered around a tube axis of the tubular member; and
a plurality of sub wires each connecting adjacent ones of the plurality of main wires to each other,
wherein each of the plurality of main wires is configured to curve when the retriever is expanded such that a space having a predetermined size is provided by the plurality of main wires,
wherein each of the plurality of sub wires is directly connected to an intermediate portion of a corresponding main wire of the plurality of main wires in an axial direction of the retriever,
wherein each of the plurality of sub wires is configured to be foldable at at least one point between the adjacent ones of the plurality of main wires,
wherein, when the retriever is expanded, folding points of the plurality of sub wires are positioned inside the space such that the plurality of sub wires do not protrude out of the plurality of main wires,
wherein the retriever further comprises a plurality of regulating portions connected to the folding points of the plurality of sub wires to regulate positions of the folding points such that, when the retriever is expanded, the folding points do not protrude out of the plurality of main wires,
wherein each of the plurality of sub wires is configured to be foldable such that a pair of arm portions extending away from each other from the folding point toward the adjacent ones of the plurality of main wires move toward each other, and is arranged to be convex from an intermediate portion of the retriever toward an end portion of the retriever, and
wherein each of the plurality of regulating portions connects the folding point of a corresponding one of the plurality of sub wires and the end portion of the retriever to each other.

2. The foreign substance removing device according to claim 1, wherein a rigidity of the plurality of main wires is higher than a rigidity of the plurality of sub wires.

3. A foreign substance removing device for removing a foreign substance in a body lumen, the foreign substance removing device comprising:
a tubular member; and
a retriever disposed in a portion of the tubular member and configured to be expandable to and contractible from a predetermined shape,
wherein the retriever comprises:
a plurality of main wires disposed to be centered around a tube axis of the tubular member; and
a plurality of sub wires each connecting adjacent ones of the plurality of main wires to each other,
wherein each of the plurality of main wires is configured to curve when the retriever is expanded such that a space having a predetermined size is provided by the plurality of main wires,
wherein each of the plurality of sub wires is directly connected to an intermediate portion of a corresponding main wire of the plurality of main wires in an axial direction of the retriever,
wherein each of the plurality of sub wires is configured to be foldable at at least one point between the adjacent ones of the plurality of main wires, and
wherein, when the retriever is expanded, folding points of the plurality of sub wires are positioned inside the space such that the plurality of sub wires do not protrude out of the plurality of main wires, wherein, when the retriever is viewed from a direction orthogonal to the tube axis of the tubular member, a part of the plurality of sub wires arranged in a first region from an intermediate portion of the retriever to one end portion of the retriever and another part of the plurality of sub wires arranged in a second region from the intermediate portion of the retriever to another end portion of the retriever are symmetrical with respect to the intermediate portion of the retriever.

4. A foreign substance collecting system for collecting a foreign substance in a body lumen, the foreign substance collecting system comprising: a foreign substance removing catheter; and a foreign substance capturing catheter to capture the foreign substance in the body lumen, wherein the foreign substance capturing catheter comprises a lumen through which the foreign substance removing catheter is passed, wherein the foreign substance removing catheter comprises:

a catheter body; and a foreign substance removing device disposed at a distal portion of the catheter body, wherein the foreign substance removing device comprises:

a tubular member; and a retriever disposed in a portion of the tubular member and configured to be expandable to and contractible from a predetermined shape, wherein the retriever comprises:

a plurality of main wires disposed to be centered around a tube axis of the tubular member; and a plurality of sub wires each connecting adjacent ones of the plurality of main wires to each other, wherein each of the plurality of main wires is configured to curve when the retriever is expanded such that a space having a predetermined size is provided by the plurality of main wires, wherein each of the plurality of sub wires is directly connected to an intermediate portion of a corresponding main wire of the plurality of main wires in an axial direction of the retriever, wherein each of the plurality of sub wires is configured to be foldable at at least one point between the adjacent ones of the plurality of main wires, wherein, when the retriever is expanded, folding points of the plurality of sub wires are positioned inside the space such that the plurality of sub wires do not protrude out of the plurality of main wires, wherein the retriever further comprises a plurality of regulating portions connected to the folding points of the plurality of sub wires to regulate positions of the folding points such that, when the retriever is expanded, the folding points do not protrude out of the plurality of main wires, wherein each of the plurality of sub wires is configured to be foldable such that a pair of arm portions extending away from each other from the folding point toward the adjacent ones of the plurality of main wires move toward each other, and is arranged to be convex from an intermediate portion of the retriever toward an end portion of the retriever, and wherein each of the plurality of regulating portions connects the folding point of a corresponding one of the plurality of sub wires and the end portion of the retriever to each other.

5. The foreign substance removing device according to claim 3, wherein a rigidity of the plurality of main wires is higher than a rigidity of the plurality of sub wires.

6. A foreign substance collecting system for collecting a foreign substance in a body lumen, the foreign substance collecting system comprising:

a foreign substance removing catheter; and a foreign substance capturing catheter to capture the foreign substance in the body lumen, wherein the foreign substance capturing catheter comprises a lumen through which the foreign substance removing catheter is passed, wherein the foreign substance removing catheter comprises:

a catheter body; and a foreign substance removing device disposed at a distal portion of the catheter body, wherein the foreign substance removing device comprises:

a tubular member; and a retriever disposed in a portion of the tubular member and configured to be expandable to and contractible from a predetermined shape, wherein the retriever comprises:

a plurality of main wires disposed to be centered around a tube axis of the tubular member; and a plurality of sub wires each connecting adjacent ones of the plurality of main wires to each other, wherein each of the plurality of main wires is configured to curve when the retriever is expanded such that a space having a predetermined size is provided by the plurality of main wires, wherein each of the plurality of sub wires is directly connected to an intermediate portion of a corresponding main wire of the plurality of main wires in an axial direction of the retriever, wherein each of the plurality of sub wires is configured to be foldable at at least one point between the adjacent ones of the plurality of main wires, wherein, when the retriever is expanded, folding points of the plurality of sub wires are positioned inside the space such that the plurality of sub wires do not protrude out of the plurality of main wires, wherein, when the retriever is viewed from a direction orthogonal to the tube axis of the tubular member, a part of the plurality of sub wires arranged in a first region from an intermediate portion of the retriever to one end portion of the retriever and another part of the plurality of sub wires arranged in a second region from the intermediate portion of the retriever to another end portion of the retriever are symmetrical with respect to the intermediate portion of the retriever.

* * * * *